United States Patent [19]

Bonati

[11] 4,101,652

[45] Jul. 18, 1978

[54] PHARMACEUTICALLY ACTIVE COMPLEXES AND PHARMACEUTICAL COMPOSITIONS CONTAINING EASCIN AND STEROLS

[75] Inventor: Attilio Bonati, Milan, Italy

[73] Assignee: Inverni Della Beffa S.p.A., Milan, Italy

[21] Appl. No.: 695,752

[22] Filed: Jun. 14, 1976

[30] Foreign Application Priority Data

Jul. 1, 1975 [GB] United Kingdom ............... 27707/75

[51] Int. Cl.$^2$ ...................... A61K 31/705; C07J 17/00
[52] U.S. Cl. ...................................... 424/49; 424/182; 536/4; 536/5
[58] Field of Search ................. 424/182, 49, 180, 243; 536/4, 5, 6, 7

[56] References Cited

U.S. PATENT DOCUMENTS

| | | | |
|---|---|---|---|
| 3,170,916 | 2/1965 | Dziengel | 536/5 |
| 3,839,317 | 10/1974 | Higuchi | 424/182 |
| 3,966,918 | 6/1976 | Kawamata et al. | 536/5 |

FOREIGN PATENT DOCUMENTS

1,217,547  5/1966  Fed. Rep. of Germany ........... 536/5

OTHER PUBLICATIONS

Kondo, "Chem. Abst." vol. 24, 1930, p. 5868.

*Primary Examiner*—Johnnie R. Brown
*Attorney, Agent, or Firm*—Browdy & Neimark

[57] ABSTRACT

Complexes of saponins with sterols are disclosed which possess the pharmaceutical activity of the free saponins, but which have reduced side-effects. Also disclosed are pharmaceutical compositions containing the complexes.

19 Claims, No Drawings

PHARMACEUTICALLY ACTIVE COMPLEXES AND PHARMACEUTICAL COMPOSITIONS CONTAINING EASCIN AND STEROLS

This invention relates to pharmaceutically active complexes and to pharmaceutical compositions containing those complexes.

A number of saponins (a class of glycosides obtainable from a wide range of plant tissues) are endowed with valuable pharmacological activity. However, in many instances the saponins are highly toxic or give rise to undesirable side effects on administration, hence drastically limiting their usefulness. Thus, for example, aescin, the principal saponin of *Aesculus hippocastanum*, has valuable pharmacological activity, particularly as an anti-inflammatory, anti-oedemagenic and vaso-protective agent. However, aescin acts as an irritant when brought into contact with many tissues, particularly mucous membranes and this characteristic limits its use, particularly for local application.

We have now discovered that certain complexes of saponins have reduced toxicity compared to the free saponins, but still retain useful pharmacological activity.

Thus according to one aspect of the present invention there are provided pharmaceutical compositions comprising a complex of a saponin and a sterol, particularly a sterol having a hydroxyl group at the 3-position, and a pharmaceutically acceptable diluent or carrier. The complexes contained as active ingredient in the compositions of the invention may be formed between a single saponin and a single sterol, or between more than one of either or both components.

Examples of saponins which form complexes with sterols are aescin, the Polygala saponins, tomatin and digitonin and examples of suitable sterols are cholesterol, β-sitosterol, stigmasterol campesterol and mixtures thereof. Preferably, on account of its ready availability in pure form, the sterol used in forming the complex with the saponin is cholesterol. Certain saponins contain groups capable of forming salts, e.g. COOH groups and the complexes contained in the pharmaceutical compositions of the invention may be formed from either the free form of the saponin or from a pharmaceutically acceptable salt. Accordingly, the term "saponin" as used herein is intended to embrace both the free forms and pharmaceutically acceptable salts of those saponins capable of salt-formation.

Thus, for example, the saponin aescin may be represented in its free acid form by the formula

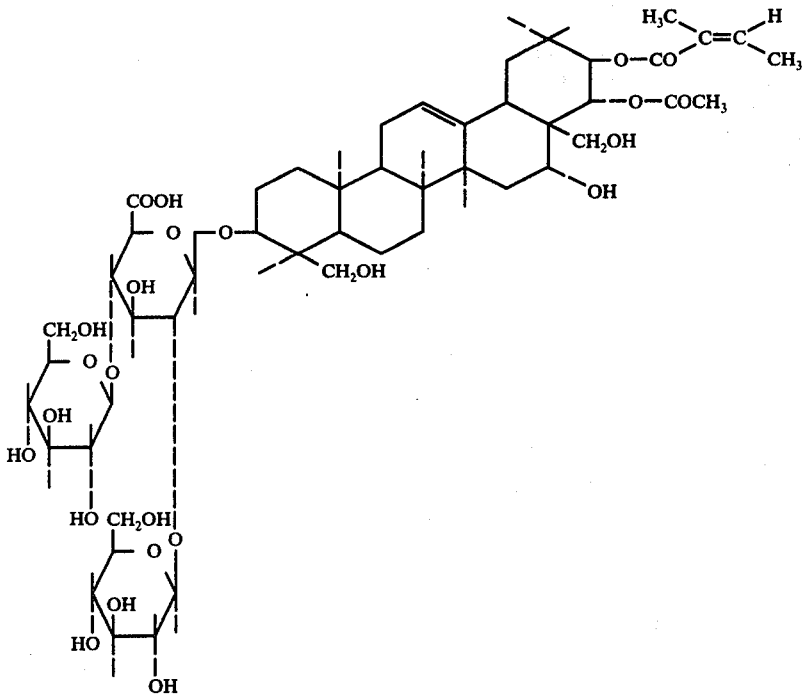

Aescin is generally obtained in the form of a sodium or potassium salt from the seeds of Aesculus hippocastanum by extraction with alcohol or some other neutral organic solvent. These salts may be converted to the free acid form of aescin (as shown in the above formula) by treatment with an acid or an ion exchange resin and the so-formed free acid form may be converted to other pharmaceutically acceptable salts by known salification techniques. Any of these forms of aescin (i.e. the free form or pharmaceutically acceptable salts, e.g. the sodium or potassium salts) may be used to form the complexes contained in the pharmaceutical compositions of the invention and generally, the yield of complex is not affected by the form of aescin used.

Apart from the complexes formed between cholesterol and the raw or unpurified sodium and potassium forms of aescin, the complexes formed between sterols and aescin (in free acid form or in the form of a pharmaceutically acceptable salt) are novel and form a further aspect of the present invention.

Examples of such novel complexes include those formed between the free acid form of aescin and cholesterol, between aescin (in free acid form or in the form of a pharmaceutically acceptable salt) and at least one sterol selected from β-sitosterol, stigmasterol and campesterol and between the purified sodium and potassium forms of aescin and cholesterol. The novels complexes may be formed between aescin and the individual sterols and between aescin and mixtures of sterols, e.g. mixtures of β-sitosterol, stigmasterol and campesterol.

The complexes contained as active ingredient in the pharmaceutical compositions of the invention may be prepared by contacting the saponin and the sterol, preferably in the presence of a solvent for one or both of the saponin and the sterol, and recovering the complex. The weight ratio between the saponin and the sterol is not unduly critical but preferably is within the range from 3:7 to 6:4.

Although the complexes may be formed by reacting the saponins with the sterol in a relatively impure state (i.e. in the raw state in which it is isolated from its natural source) preferably, the sterol is reacted with a purified form of the saponin. Thus, in order to ensure that the pharmaceutical compositions formed from the complexes are suitable for pharmaceutical administration, the sterol is preferably contacted with a purified form of the saponin, i.e. the saponin is preferably isolated from its natural source and subjected to one or more conventional purification procedures (for example chromatographic separation or fractional crystallisation) before being converted to the required complex.

It is not necessary to utilise a highly purified form of the sterol in the production of the complexes and for example both pure and commercial grades of β-sitosterol may be used. The latter usually consist of mixtures of β-sitosterol and campesterol or mixtures of β-sitosterol, campesterol and stigmasterol in various ratios. There are frequently economic advantages in using commercial grades of sterol.

On account of their particularly valuable pharmaceutical properties, the preferred complexes contained in the pharmaceutical compositions of the invention are complexes of aescin and a sterol, particularly cholesterol or β-sitosterol. These complexes, in which the saponin and sterol are generally present in a weight ratio of approximately 1:1, but which may vary from 3:7 to 6:4 are endowed with the anti-inflammatory, anti-oedemagenic and vaso-protective activity of aescin alone but give rise to substantially no local irritative phenomena. Accordingly, they are particularly suitable for formulating into pharmaceutical compositions adapted for local application, e.g. ointments, gels and medicated dentifrices. Although formation of the complex between aescin and cholesterol has been described as a means for extracting aescin from aqueous solutions, the advantageous pharmacological properties of the complex have never been hitherto described.

A lack of irritative phenomena may be observed not only when the compositions are applied topically, for example as ointments, gels or aqueous suspensions, but also when administered intraperitoneally or directly into a joint, for example a knee joint.

Examples of galenic forms of the compositions of the invention include sterile liquids suitable for parenteral administration, shaped dosage units, forms suitable for rectal administration (e.g. suppositories) forms suitable for topical administration (e.g. ointments, creams, gels, and aqueous suspensions), and dentifrices.

In formulating compositions according to the invention, a wide range of excipients may be used, the nature of which will depend, of course, on the intended mode of application of the composition. Examples include preservatives and buffering, thickening, suspending, stabilising, wetting, emulsifying, colouring and flavouring agents and in particular carboxy vinyl polymers, propylene glycol, ethyl alcohol, water, cetyl alcohol, saturated vegetable triglycerides, fatty acid esters of propylene glycol, triethanolamine, glycerol, starch, sorbitol, bentonite, carboxymethyl cellulose, lauryl sulphate, dicalcium phosphate powdered silicia etc. Frequently, more than one diluent or carrier is advantageously used.

The results of some pharmacological tests are given below which illustrate the properties of complexes of aescin with cholesterol and β-sitosterol.

1. Carragenin-induced Oedema in the Paw of the Rat (a) Male rats of average weight 140 g. were fasted (with water ad libitum) for the 16 hours prior to the administration of carragenin.

Half an hour prior to the administration of 0.1 ml. of a 1% carragenin solution in the sub-plantar region of the rat's paw, aescin, cholesterol/aescin complex and cholesterol, dissolved or suspended in an aqueous 2% solution of carboxy methyl cellulose, were administered intraperitoneally to respective groups of rats. The aescin was in the form of the potassium salt and the potassium salt of aescin was used to form the aescin/cholesterol complex.

From Table 1 below it can be seen that the anti-oedemagenic activity of aescin and of the cholesterol/aescin complex are practically equal.

Table 1

| Treatment (1) | mg/kg | No. of animals | Volume of Oedema (ml) | Percentage Inhibition |
|---|---|---|---|---|
| Controls (2% carboxy methyl cellulose) | — | 12 | 0.60 ± 0.005 | — |
| Aescin | 0.5 | 12 | 0.45 ± 0.015* | 24.3 |
| Aescin | 2.0 | 12 | 0.29 ± 0.010* | 51.2 |
| Cholesterol/aescin complex | 1.0 | 12 | 0.46 ± 0.10* | 23.3 |
| Cholesterol/aescin complex | 4.0 | 12 | 0.31 ± 0.007* | 48.0 |
| Cholesterol | 0.5 | | 0.59 ± 0.003 | — |
| Cholesterol | 2.0 | | 0.56 ± 0.007 | 6.6 |

(1) The substances were administered intraperitoneally in solution or suspension in 2% aqueous solution of carboxymethyl cellulose, at the rate of 1 ml./hg.
*Significantly different from the controls (P <0.05) according to Duncan's test.

(b) Male rats of average weight 140 g. were fasted for 16 hours, with water ad libitum.

0.1 ml. of a 1% solution of carragenin in physiological solution were injected into the sub-plantar zone of the rat's paw; immediately afterwards 50 mg. (equal to 0.5 mg. of aescin per rat) of an ointment containing 2% of a complex formed between cholesterol and the free acid form of aescin was applied to the paw.

The anti-oedematous activity of the topically applied cholesterol/aescin complex is apparent from Table 2.

Table 2

| Treatment | No. of animals | Volume of Oedema (ml) | Percentage Inhibition |
|---|---|---|---|
| Controls (1) | 10 | 0.54 ± 0.06 | — |
| Ointment with cholesterol/aescin complex (50 mg) | 10 | 0.40 ± 0.01* | 25.9 |

(1) Treated with 50 mg. of an ointment containing only excipients.
*Significantly (P <0.01) different from the controls according to Student's "t" test.

(c) Male rats of average weight 140 g. were fasted (with water ad libitum) for 16 hours prior to treatment.

0.1 ml. of a 1% solution of carragenin either alone or containing, in suspension, aescin in the form of the sodium salt (0.1 and 0.2 mg.) or a complex formed between β-sitosterol and the sodium form of aescin (0.2 or 0.4 mg.), were injected into the sub-plantar region of the paw.

From Table 3 it is apparent that, while aescin has a local irritant action which causes an increase of oedema compared with the controls treated with carragenin alone, the β-sitosterol/aescin complex has no irritant action and, at a dose of 0.4 mg., causes a significant reduction of the oedema compared with the controls.

Table

| Treatment | No. of animals | Volume of Oedena (ml) | Percentage variation of the Oedema |
|---|---|---|---|
| Controls (0.1 ml. solution A) (1) | 20 | 0.59 ± 0.01 | |
| Solution A + 0.1 mg of aescin | 10 | 0.70 ± 0.02* | +18.6 |
| Solution A + 0.2 mg of aescin | 10 | 0.73 ± 0.01* | +23.7 |
| Solution A + 0.2 mg of β-sitosterol/aescin complex | 10 | 0.51 ± 0.01** | −13.5 |
| Solution A + 0.4 mg of β-sitosterol/aescin complex | 10 | 0.40 ± 0.02** | −32.2 |

(1) Solution A: 1% carragenin in physiological solution
*Significantly different (as an increase) from the controls (P <0.05) according to Student's "t" test.
**Significantly different (as a reduction) from the controls (P <0.05) according to Student's "t" test.

2. TOLERANCE 2 mg of a complex formed between the sodium salt of aescin and cholesterol, 2 mg. of a complex formed between the sodium salt of aescin and β-sitosterol and 1 mg. of the sodium salt of aescin, suspended in 0.1 mg. of physiological solution (0.9% sodium chloride) were injected into the knee joint of the right rear leg of respective New Zealand male albino rabbits (app. 2 kg. weight).

Groups of three rabbits were used for each of the three substances under examination.

The joint tissues were examined six hours after the intra-articular injection, and revealed the presence of oedematous liquid in all the animals treated with aescin while no inflammatory or irritative phenomena of any kind whatever were noted in those treated with the two complexes.

Some examples of pharmaceutical formulations are set forth below:

| | | |
|---|---|---|
| Gel | | |
| Cholesterol/aescin (free acid) complx 5:5 weight ratio | 2 | g |
| Excipients (carboxy vinyl polymer, propylene glycol, sodium hydroxide, ethyl alcohol, purified water) q.s. | 100 | g |
| Gel | | |
| Cholesterol/aescinn (free acid) complex 6:4 weight ratio | 2 | g |
| Ruscogenins | 1 | g |
| Excipients (carbody vinyl polymer, propylene glycol, tween 20, ethyl alcohol) q.s. | 100 | g |
| Ointment | | |
| β-sitosterol/aescin (sodium salt) complex 6:4 weight ratio | 2 | g |
| Excipients (cetyl alcohol, saturated vegetable triglycerides, fatty acid esters from $C_{12}$ to $C_{14}$ with polyethylene glycol, carboxy vinyl polymer triethanolamine, glycerine, purified water) q.s. | 100 | g |
| Ointment | | |
| Cholesterol/aescin (free acid) complex 7:3 weight ratio | 2 | g |
| Glycyrrhetic acid | 1 | g |
| Ruscogenins | 1 | g |
| Excipients (polyethylene glycol 4000, propylene glycol, tween 20, cetyl alcohol, purified water) q.s. | 100 | g |
| Ointment | | |
| β-sitosterol/aescin (free acid) complex 6:4 weight ratio | 2 | g |
| Total flavanol oligommers of Aesculus Hippocastanum | 5 | g |
| Excipients (tween 80, spermaceti, stearin, fatty acid sodium lauryl sulfate, hydrogenated lanolin, sodium alginate, purified water) q.s. | 100 | g |
| Suppositories | | |
| Cholesterol/aescin (potassium salt) complex 5:5 weight ratio | 20 | mg |
| Excipients (starch, saturated vegetable oils, hydrogenated vegetable triglycerides) q.s. | 1.5 | g |
| Suppositories | | |
| Cholesterol/aescin (free acid) commmplex 5:5 weight ratio | 10 | mg |
| Ruscogenins | 10 | mg |
| Excipients (hydrogenated vegetable triglycerides) q.s. | 1.5 | g |
| Suppositories | | |
| β-sitosterol/aescin (free acid) complex 6:4 weight ratio | 20 | mg |
| Excipients (polyethylene glycol 400, polyethylene glycol 6000) q.s. | 1.5 | g |
| Suppositories | | |
| Technical β-sitosterol/aescin (free acid) complex 6:4 weight ratio | 10 | mg |
| Ruscogenins | 10 | mg |
| Excipients (polyethylene glycol 400, polyethylene glycol 6000) q.s. | 1.5 | g |
| Dentifrice | | |
| Cholesterol/aescin (sodium salt) complex 5:5 weight ratio | 2 | g |
| Excipients (glycerine, 70 per cent sorbitol, bentonite, carboxy methyl cellulose, lauryl sulphate, dicalcium phosphate, powdered silica, purified water) q.s. | 100 | g |
| Dentifrice | | |
| Cholesterol/aescin (sodium salt) complex 6:4 weight ratio | 2 | g |
| Glycyrrhetic acid | 0.5 | g |

| Excipients (propylene glycol, starch, glycerine aluminium hydroxide, calcium phosphate, powdered silica, titanium dioxide, lauryl sulphate, glycamil, purified water) q.s. | 100 g |
| --- | --- |

The production of complexes of aescin with various sterols will now be described in the following Examples 1, 2 and 3.

EXAMPLE 1

Dissolve 15 g of purified aescin (potassium salt) in 225 ml of 50 percent aceton containing 15 g of cholesterol.

Heat under stirring at reflux for 4 hours, cool and then allow to stand overnight.

Filter the complex, wash with 15 ml of 50 percent acetone and 15 ml of anhydrous acetone.

Dry in vacuo overnight at 60° C.

Yield: 22 g of product containing about 11 g of aescin and 11 g of cholesterol.

EXAMPLE 2

Dissolve 15 g of purified aescin (sodium salt) in 150 ml of 80 percent ethanol. Add 15 g of β-sitosterol dissolved in 50 ml of ethyl ether.

Evaporate the ethyl ether and heat the remaining suspension at 50° C. for 4 hours, under stirring.

Evaporate in vacuo at low temperature to 50 ml, then allow to stand at room temperature overnight.

Filter, wash the obtained product with 15 ml of 50 percent ethanol and dry in vacuo at 50° C. for 48 hours.

Yield: 20 g of product containing about 10 g of aescin and 10 g of β-sitosterol.

EXAMPLE 3

Dissolve 15 g of purified aescin (free acid) in 150 ml of 80 percent ethanol. Add 15 g of technical β-sitosterol (mixture of β-sitosterol, stigmasterol and campesterol) in 60 ml of methylene chloride.

Evaporate the methylene chloride and heat the remaining suspension at 50° C for 4 hours, under stirring.

Evaporate in vacuo at low temperature to 50 ml, then allow to stand at room temperature overnight.

Filter, wash the obtained product with 15 ml of 50 percent ethanol and dry in vacuo at 50°-60° C. for 48 hours.

Yield: 22 g of product containing about 8 g of aescin and 14 g of sterols.

It will be appreciated that the compositions of the invention can be used in the human and veterinary therapeutic field, in the treatment of (in the case of the aescin complexes) inflammatory states and of states of impairment of the capillary permeability.

I claim:

1. A pharmaceutical composition comprising a pharmaceutically acceptable diluent or carrier and as active ingredient an effective amount of a complex formed between aescin and a sterol selected from the group consisting of cholesterol, β-sitosterol, stigmasterol, campesterol and mixtures thereof, the aescin being in free acid form or in the form of a pharmaceutically acceptable salt, with the proviso that where the composition is an unpurified aqueous suspension of a complex formed between cholesterol and the impure sodium or potassium forms of aescin, the composition contains an ingredient selected from the group consisting of preservatives and buffering, thickening, suspending, stabilizing, wetting, emulsifying, coloring and flavoring agents.

2. A composition according to claim 1 containing as active ingredient an effective amount of a complex formed between cholesterol and aescin, the aescin being in free acid form or the form of a pharmaceutically acceptable salt.

3. A composition according to claim 1 containing as active ingredient an effective amount of a complex formed between β-sitosterol and aescin, the aescin being in free acid form or the form of a pharmaceutically acceptable salt.

4. A composition according to claim 1 comprising a diluent or carrier selected from the group consisting of carboxy vinyl polymers, propylene glycol, ethyl alcohol, water, cetyl alcohol, saturated vegetable triglycerides, fatty acid esters of propylene glycol, triethanolamine, glycerol, starch, sorbitol, bentonite, carboxymethyl cellulose, lauryl sulphate, dicalcium phosphate and powdered silica.

5. A composition according to claim 1 comprising at least two diluents or carriers.

6. A composition according to claim 1 in the form of a sterile liquid suitable for parenteral injection.

7. A composition according to claim 1 in the form of a shaped dosage unit.

8. A composition according to claim 1 in the form of a suppository.

9. A composition according to claim 1 in a form adapted for topical application.

10. A composition according to claim 9 in the form of an ointment, cream, gel or aqueous suspension.

11. A composition according to claim 1 in the form of a dentifrice.

12. A complex formed between aescin and at least one sterol selected from the group consisting of cholesterol, β-sitosterol, stigmasterol, campesterol and mixtures thereof, the asecin being in free acid form or in the form of a pharmaceutically acceptable salt, with the proviso that where the sterol is cholesterol, the aescin is in the free acid form or in the form of a salt other than a sodium or potassium salt.

13. A complex according to claim 12 formed between aescin and β-sitosterol, the aescin being in free acid form or in the form of a pharmaceutically acceptable salt.

14. A complex according to claim 12 formed between aescin and stigmasterol, the aescin being in free acid form or in the form of a pharmaceutically acceptable salt.

15. A complex according to claim 12 formed between aescin and campesterol, the aescin being in free acid form or in the form of a pharmaceutically acceptable salt.

16. A process for producing an antiinflammatory effect in an animal which comprises administering to said animal an anti-inflammatory effective quantity of a complex formed between aescin and a sterol selected from the group consisting of cholesterol, β-sitosterol, campesterol and mixtures thereof, the aescin being in free acid form or in the form of a pharmaceutically acceptable salt.

17. A method of inducing an anti-oedemagenic effect in an animal which comprises administering to said animal an anti-oedemagenic effective quantity of a complex formed between aescin and a sterol selected from the group consisting of cholesterol, β-sitosterol, stigmasterol, campesterol and mixtures thereof, the aescin being in free acid form or in the form of a pharmaceutically acceptable salt.

18. A method of inducing a vaso-protective effect in an animal which comprises administering to said animal a vaso-protective effective quantity of a complex formed between aescin and a sterol selected from the group consisting of cholesterol, β-sitosterol, stigmasterol, campesterol and mixtures thereof, the aescin being in free acid form or in the form of a pharmaceutically acceptable salt.

19. A composition according to claim 1 comprising a purified aqueous suspension containing as an active ingredient an effective amount of the complex formed between cholesterol and the sodium or potassium salt of aescin.

* * * * *